United States Patent [19]

Plank et al.

[11] 4,076,842

[45] Feb. 28, 1978

[54] CRYSTALLINE ZEOLITE ZSM-23 AND SYNTHESIS THEREOF

[75] Inventors: Charles J. Plank, Woodbury; Edward J. Rosinski, Pedricktown, both of N.J.; Mae K. Rubin, Bala Cynwyd, Pa.

[73] Assignee: Mobil Oil Corporation, New York, N.Y.

[21] Appl. No.: 739,414

[22] Filed: Nov. 8, 1976

Related U.S. Application Data

[63] Continuation-in-part of Ser. No. 585,632, Jun. 10, 1975, abandoned.

[51] Int. Cl.$^2$ .............................................. C01B 33/28
[52] U.S. Cl. ................................ 423/328; 252/455 Z; 260/326.61; 423/329
[58] Field of Search ...................... 423/328, 329, 330; 252/455 Z, 431 N; 260/326.61, 567.6 R, 567.6 M, 567.6 P, 583 R, 448 C

[56] References Cited

U.S. PATENT DOCUMENTS

| | | | |
|---|---|---|---|
| 3,702,886 | 11/1972 | Argauer et al. | 423/328 |
| 3,709,979 | 1/1973 | Chu | 423/328 |
| 3,832,449 | 8/1974 | Rosinski et al. | 423/328 |
| 3,950,496 | 4/1976 | Ciric | 423/328 |
| 3,972,983 | 8/1976 | Ciric | 423/328 |
| 4,016,245 | 4/1977 | Plank et al. | 423/328 |

*Primary Examiner*—Edward J. Meros
*Attorney, Agent, or Firm*—Charles A. Huggett; Dennis P. Santini

[57] ABSTRACT

A new crystalline zeolite, designated ZSM-23, a method of making same and the use thereof in catalytic conversion of organic compounds is the subject of this application. The new zeolite has a composition, in the anhydrous state, expressed in terms of mole ratios of oxides, as follows;

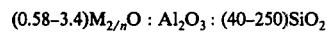

$$(0.58-3.4)M_{2/n}O : Al_2O_3 : (40-250)SiO_2$$

wherein M is at least one cation having a valence n, and is characterized by a specified X-ray powder diffraction pattern.

21 Claims, No Drawings

CRYSTALLINE ZEOLITE ZSM-23 AND SYNTHESIS THEREOF

CROSS-REFERENCE TO RELATED APPLICATION

This is a continuation-in-part of application Ser. No. 585,632, filed June 10, 1975, now abandoned.

BACKGROUND OF THE INVENTION

1. Field of the Invention

This invention relates to a novel crystalline aluminosilicate, to a method for its preparation and to its use in catalytic conversion or organic compounds.

2. Description of the Prior Art.

Zeolitic materials, both natural and synthetic, have been demonstrated in the past to have catalytic properties for various types of hydrocarbon conversions. Certain zeolitic materials are ordered, porous crystalline aluminosilicates having a definite crystalline structure within which there are a large number of smaller cavities which may be interconnected by a number of still smaller channels. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline aluminosilicates. These aluminosilicates can be described as a rigid three-dimensional framework of $SiO_4$ and $AlO_4$ in which the tetrahedra are cross-linked by the sharing of oxygen atoms whereby the ratio of the total aluminum and silicon atoms to oxygen is 1:2. The electrovalence of the tetrahedra containing aluminum is balanced by the inclusion in the crystal of a cation, for example, alkali metal or an alkaline earth metal cation. This can be expressed wherein the ratio of aluminum to the number or various cations, such as Ca, Sr, Na, K or Li is equal to unity. One type of cation may be exchanged either entirely or partially by another type of cation utilizing ion exchange techniques in a conventional manner. By means of such cation exchange, it has been possible to vary the properties of a given aluminosilicate by suitable selection of the cation. The spaces between the tetrahedra are occupied by molecules of water prior to dehydration.

Prior art techniques have resulted in the formation of a great variety of synthetic aluminosilicates. These aluminosilicates have come to be designated by letter or other convenient symbols, as illustrated by zeolite A (U.S. Pat. No. 2,882,243), zeolite X (U.S. Pat. No. 2,882,244), zeolite Y (U.S. Pat. No. 3,130,007), zeolite ZK-5 (U.S. Pat. No. 3,247,195), zeolite ZK-4 (U.S. Pat. No. 3,314,752) and zeolite ZSM-5 (U.S. Pat. No. 3,702,886) merely to name a few.

SUMMARY OF THE INVENTION

The present invention relates to a novel synthetic crystalline aluminosilicate, hereinafter designated "zeolite ZSM-23" or simply "ZSM-23", to methods for its preparation and to the conversion of organic compounds conducted therewith. The ZSM-23 composition has a characteristic X-ray diffraction pattern, the values of which are set forth in Table I, hereinafter. The ZSM-23 composition can also be identified, in terms of mole ratios of oxides and in the anhydrous state, as follows:

$$(0.58-3.4)M_{2/n}O : Al_2O_3 : (40-250)SiO_2$$

wherein M is at least one cation and n is the valence thereof. It will be noticed that the ratio of $M_{2/n}O$ may exceed unity in this material. This is probably due to the occlusion of excess organic species, used in the preparation of ZSM-23, within the zeolite pores.

In a preferred synthesized form, the zeolite has a formula, in terms of mole ratios of oxides and in the anhydrous state, as follows:

$$(0.5-3.0)R_2O : (0.08-0.4)M_2O : Al_2O_3 : (40-250)SiO_2$$

wherein R is a nitrogen-containing organic cation and M is an alkali metal cation. It will be noticed that in this preferred form the ratio of $R_2O$ to $Al_2O_3$ may exceed unity, probably due to the occlusion of excess nitrogen-containing organic species ($R_2O$) within the zeolite pores.

In a preferred synthesized form, the zeolite has a formula, in terms of mole ratios of oxides and in the anhydrous state, as follows:

$$(0.7-2.8)R_2O : (0.08-0.25)M_2O : Al_2O_3 : (50-220)SiO_2$$

wherein R is a nitrogen-containing organic cation, such as, for example, that derived from pyrrolidine and M is an alkali metal cation, especially sodium.

The original cations of the as synthesized ZSM-23 can be replaced in accordance wih techniques well known in the art, at least in part, by ion exchange with other cations. Preferred replacing cations include metal ions, ammonium ions, hydrogen ions and mixtures thereof. Particularly preferred cations are those which render the zeolite catalytically active especially for hydrocarbon conversion. These include hydrogen, rare earth metals, aluminum metals of Groups IIA, IIIB, IVD, VIII, IB, IIB, IIIA, IVA.

The synthetic ZSM-23 zeolite possesses a definite distinguishing crystalline structure whose X-ray diffraction pattern shows substantially the significant lines set forth in Table I.

TABLE I

| d(A) | $I/I_o$ |
| --- | --- |
| 11.2 ± 0.23 | Medium |
| 10.1 ± 0.20 | Weak |
| 7.87 ± 0.15 | Weak |
| 5.59 ± 0.10 | Weak |
| 5.44 ± 0.10 | Weak |
| 4.90 ± 0.10 | Weak |
| 4.53 ± 0.10 | Strong |
| 3.90 ± 0.08 | Very Strong |
| 3.72 ± 0.08 | Very Strong |
| 3.62 ± 0.07 | Very Strong |
| 3.54 ± 0.07 | Medium |
| 3.44 ± 0.07 | Strong |
| 3.36 ± 0.07 | Weak |
| 3.16 ± 0.07 | Weak |
| 3.05 ± 0.06 | Weak |
| 2.99 ± 0.06 | Weak |
| 2.85 ± 0.06 | Weak |
| 2.54 ± 0.05 | Medium |
| 2.47 ± 0.05 | Weak |
| 2.40 ± 0.05 | Weak |
| 2.34 ± 0.05 | Weak |

These values were determined by standard technique. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, 100 I/Io, where Io is the intensity of the strongest line or peak, and d (obs.), the interplanar spacing in Angstrom units, corresponding to the recorded lines, were calculated. It should be understood that this X-ray diffraction pattern is characteristic of all the species of ZSM-23 compositions. Ion exchange of the sodium ion with cations reveals substantially the same pattern with some minor shifts in interplanar spacing and variation in relative intensity. Other minor variations can occur depending on the silicon to aluminum ratio of the perpendicular sample, as well as if it has previously been subjected to thermal treatment.

While synthetic ZSM-23 zeolites may be used in a wide variety of organic compound conversion reactions, they are notably useful in the processes of polymerization, aromatization, reforming, esterification and cracking. Other hydrocarbon conversion processes for which ZSM-23 may be utilized in one or more of its active forms include, for example, hydrocracking and converting light aliphatics to aromatics such as in U.S. Pat. No. 3,760,024.

Synthetic ZSM-23 zeolites can be used either in the alkali metal containing form, the alkali metal form and hydrogen form or another univalent or multivalent cationic form. They can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Combinations of the aforenoted metals may also be used. Such components can be exchanged into the composition, impregnated thereon or physically intimately admixed therewith. Such components can be impregnated in or on to ZSM-23 such as, for example, by, in the case of platinum, treating the zeolite with a platinum metal-containing ion. Thus, suitable platinum compounds for this purpose include chloroplatinic acid, platinous chloride and various compounds containing the platinum amine complex. Combinations of metals and methods for their introduction can also be used.

As prepared, R can be a cation derived from pyrrolidine present in a quantity not less than 70 percent of the cation content.

M can be one or more or a variety of alkali metal cations, suitably defined as including all alkali metal ions derived from alkali metal oxide or hydroxide as well as alkali metal ions included in alkali metal silicates and aluminates (not including alkali metal salts such as sodium chloride or sodium sulfate which may be derived from neutralization of added inorganic acids such as HCl or $H_2SO_4$ or acid salts such as $Al_2(SO_4)_3$). Non-limiting examples of such suitable alkali meal ions include sodium and potassium.

Synthetic ZSM-23, when employed either as an adsorbent or as a catalyst in a hydrocarbon conversion process, should be dehydrated at least partially. This can be done by thermal treatment, i.e. heating, to a temperature in the range of 50° C to about 900° C in an inert temperature, such as air, nitrogen, etc. and at atmospheric or subatmospheric pressures for between 1 and 48 hours. Dehydration can also be performed at lower temperature merely be placing the catalyst in a vacuum, but a longer time is required to obtain a sufficient amount of dehydration.

Zeolite ZSM-23 can be suitably prepared by preparing a solution containing sources of an alkali metal oxide, preferably sodium oxide, sources of nitrogen-containing cation, preferably pyrrolidine, an oxide of aluminum, an oxide of silicon and water having a composition, in terms of mole ratios of oxides, falling within the following ranges:

$R+/R++ M+)$ : 0.85–0.95
$OH^-/ SiO_2$: 0.01–0.049
$H_2O/OH^-$: 200–600
$SiO_2/ Al_2O_3$: 55–70 wherein R is an organic nitrogen-containing cation and M is an alkali metal ion, and maintaining the mixture until crystals of the zeolite are formed. (The quantity of $OH^-$ is calculated only from the inorganic sources of alkali without any organic base contribution). Thereafter, the crystals are separated from the liquid and recovered. Typical reaction conditions consist of heating the foregoing reaction mixture to a temperature above 280° F to about 400° F for a period of time of from about 6 hours to about 14 days. A more preferred temperature range is from about 300°F to about 375°F with the amount of time at a temperature in such range being from about 24 hours to about 11 days.

The digestion of the gel particles is carried out until crystals form. The solid product is separated from the reaction medium, as by cooling the whole to room temperature, filtering and water washing.

The crystalline product is dried, e.g. at 230°F, for from about 8 to 24 hours. Of course, milder conditions may be employed if desired, e.g. room temperature under vacuum.

The composition for the synthesis of synthetic ZSM-23 can be prepared utilizing materials which can supply the appropriate oxide. Such compositions include alumintes, alumina, silicates, silica hydrosol, silica gel, silicic acid and hydroxides. It will be understood that each oxide component utilized in the reaction mixture for preparing ZSM-23 can be supplied by one or more essentail reactants and they can be mixed together in any order. For example, any oxide can be supplied by an aqueous solution, sodium hydroxide or by an aqueous solution of a suitable silicate; the cation derived from pyrrolidine can be either supplied by pyrrolidine or a salt thereof. The reaction mixture can be prepared either batchwise or continuously. Crystal size and crystallization time of the ZSM-23 composition will vary with the nature of the reaction mixture employed.

DESCRIPTION OF SPECIFIC EMBODIMENTS

As above mentioned, synthetic ZSM-23 can have the original cations associated therewith replaced by a wide variety of other cations according to techniques well known in the art. Typical replacing cations include hydrogen, ammonium and metal cations including mixtures thereof. Of the replacing metallic cations, particular preference is given to cations of metals such as rare earth, Mn, Ca, Mg, Zn, Cd, Pd, Ni, Co, Ti, Al, Sn, Fe and Co.

Typical ion exchange techniques would be to contact the synthetic ZSM-23 zeolite with a salt of the desired replacing cation or cations. Although a wide variety of salts can be employed, particular preference is given to chlorides, nitrates and sulfates.

Representative ion exchange techniques are disclosed in a wide variety of patents including U.S. Pat. Nos. 3,140,249; 3,140,251; and 3,140,253.

Following contact with the salt solution of the desired replacing cation, the zeolite is then preferably washed with water and dried at a temperature ranging from 50° C to about 300° C and thereafter may be calcined in air or other inert gas at from about 200° C to a temperature below the zeolite decomposition temperature, preferably about 900° C, for periods of time ranging from 1 to 48 hours or more to produce a catalytically-active thermal decomposition product thereof.

Regardless of the cations replacing the alkali metal in the synthesized form of the ZSM-23, the spacial arrangement of the aluminum, silicon and oxygen atoms which form the basic crystal lattices of ZSM-23 remains essentially unchanged by the described replacement of alkali metal as determined by taking an X-ray powder diffraction pattern of the ion-exchanged material.

The aluminosilicate prepared by the instant invention is formed in a wide variety of particle sizes. Generally speaking, the particles can be in the form of a powder, a granule, or a molded product, such as extrudate having particle size sufficient to pass through a 2 mesh (Tyler) screen and be retained on a 400 mesh (Tyler) screen. In cases where the catalyst is molded, such as by extrusion, the aluminosilicate can be extruded before drying or dried or partially dried and then extruded.

In the case of many catalysts, it is desired to incorporate the ZSM-23 with another material resistant to the temperatures and other conditions employed in organic conversion processes. Such matrix materials include active and inactive materials and synthetic or naturally occurring zeolites as well as inorganic materials such as clays, silica and/or metal oxides. The latter may be either naturally occurring or in the form of gelatinous precipitates, sols or gels including mixtures of silica and metal oxides. Use of a material in conjunction with the ZSM-23, i.e. combined therewith, which is active, tends to improve the conversion and/or selectivity of the catalyst in certain organic conversion processes. Inactive materials suitably serve as diluents to control the amount of conversion in a given process so that products can be obtained economically and orderly without employing other means for controlling the rate of reaction. Frequently, zeolite materials have been incorporated into naturally occurring clays, e.g. bentonite and kaolin. These materials, i.e., clays, oxides, etc., function, in part, as binders for the catalyst. It is desirable to provide a catalyst having good crush strength, because in a petroleum refinery the catalyst is often subjected to rough handling, which tends to break the catalyst down into powder-like materials which cause problems in processing.

Naturally occurring clays which can be composited with the synthetic ZSM-23 catalyst include the montmorillonite and kaolin family, which include the sub-bentonites, and the kaolins commonly known as Dixie, McNamee, Georgia and Florida clays or others in which the main mineral constituents is halloysite, kaolinite, dickite, nacrite, or anauxite. Such clays can be used in the raw state as originally mined or initially subjected to calcination, acid treatment or chemical modification.

In addition to the foregoing materials, the ZSM-23 catalyst can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used. The relative proportions of finely divided crystalline aluminosilicate ZSM-23 and inorganic oxide gel matrix vary widely with the crystalline aluminosilicate content ranging from about 1 to about 90 percent by weight and more usually in the range of about 2 to about 70 percent by weight of the composite.

In employing the ZSM-23 catalyst of this invention for polymerization of olefin containing liquid or gaseous charge stocks, such charge stocks can be polymerized at temperatures between 550° and 850° F at an hourly space velocity of between 0.5 and 50 WHSV and a pressure between 0.1 and 800 psig.

In employing the catalyst of the present invention for aromatization of gaseous or liquid charge stocks which may be olefinic or paraffinic with or without aromatics present, such stocks can be aromatized at temperatures between 800° and 1200° F and pressures from 1 to 10 atmospheres and space velocities between 0.1 and 10 WHSV.

In order to more fully illustrate the nature of the invention and the manner of practicing same, the following examples are presented.

In the examples which follow, whenever adsorption data are set forth for comparison of sorptive capacities for water, cyclohexane and n-hexane, they were determined as follows:

A weighed sample of the calcined zeolite was contacted with the desired pure adsorbate vapor in an adsorption chamber, evacuated to 12 mm when cheking capacity for water and 20 mm when checking capacity for cyclohexane and n-hexane, pressures less than the vapor-liquid equilibrium pressure of the respective adsorbate at room temperature. The pressure was kept constant (within about ± 0.5 mm) by addition of adsorbate vapor controlled by a manostat during the adsorption period which did not exceed about eight hours. As adsorbate was adsorbed by the zeolite, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample.

EXAMPLE 1

Illustrating preparation of synthetic zeolite ZSM-23, a first solution comprising 3.3 grams sodium aluminate (43.1% $Al_2O_3$, 33.1% $Na_2O$ and 24.7% $H_2O$), 30 grams $H_2O$ and 0.34 gram NaOH (50% solution with water) was prepared. Pyrrolidine in an amount of 18.2 grams was added to the first solution to form a second solution. Thereupon 164.8 grams of colloidal silica (30% $SiO_2$ and 70% $H_2O$) was added to the second solution and mixed until a homogeneous gel was formed. The gel was composed of the following components in mole ratios:

$R+/(R^+ + M^+) = 0.87$, where M is sodium and $R^+$ is the nitrogen-containing ion derived from pyrrolidine
$OH^-/SiO_2 = 0.049$ (not including any contribution of $OH^-$ from pyrrolidine)
$H_2O/OH^- = 208$ (not including any contribution of $OH^-$ from pyrrolidine)
$SiO_2/Al_2O_3 = 59.1$ The mixture was maintained at 355° F for 7 days, during which time crystallization was complete. The product crystals were filtered out of solution and water washed continuously for approximately 16 hours and thereafter dried at 230° F.

X-ray analysis of the crystalline product showed the crystals to have the following diffraction pattern:

TABLE II

| 2θ | d(A) | I/I₀ |
|---|---|---|
| 7.90 | 11.19 | 47 |
| 8.78 | 10.07 | 24 |
| 9.30 | 9.51 | 3 |
| 11.25 | 7.86 | 15 |
| 11.80 | 7.50 | 4 |
| 13.83 | 6.40 | 4 |
| 14.40 | 6.15 | 4 |
| 14.70 | 6.03 | 6 |
| 15.53 | 5.71 | 5 |
| 15.88 | 5.58 | 6 |
| 16.29 | 5.44 | 6 |
| 17.20 | 5.16 | 2 |
| 17.73 | 5.00 | 5 |
| 18.08 | 4.91 | 10 |
| 19.55 | 4.54 | 54 |
| 19.93 | 4.45 | 15 |
| 20.30 | 4.37 | 15 |
| 20.78 | 4.27 | 73 |
| 21.30 | 4.17 | 21 |
| 21.59 | 4.12 | 23 |
| 21.86 | 4.07 | 50 |
| 22.78 | 3.90 | 100 |
| 23.23 | 3.83 | 31 |
| 23.84 | 3.73 | 79 |
| 24.50 | 3.63 | 58 |
| 25.12 | 3.54 | 33 |
| 25.82 | 3.45 | 40 |
| 26.43 | 3.37 | 6 |
| 26.86 | 3.32 | 6 |
| 28.14 | 3.17 | 9 |
| 29.23 | 3.06 | 7 |
| 29.82 | 2.996 | 7 |
| 30.23 | 2.956 | 2 |
| 31.38 | 2.851 | 12 |
| 32.12 | 2.787 | 2 |
| 32.78 | 2.732 | 1 |
| 33.95 | 2.640 | 4 |
| 34.37 | 2.609 | 3 |
| 35.38 | 2.537 | 29 |
| 36.00 | 2.495 | 13 |
| 36.34 | 2.472 | 12 |
| 36.75 | 2.445 | 6 |
| 37.45 | 2.401 | 6 |
| 38.41 | 2.344 | 8 |
| 38.89 | 2.316 | 2 |
| 40.23 | 2.242 | 2 |
| 41.00 | 2.201 | 1 |
| 41.55 | 2.173 | 1 |
| 42.27 | 2.138 | 1 |
| 42.67 | 2.119 | 1 |
| 43.19 | 2.095 | 2 |
| 43.55 | 2.078 | 4 |
| 43.95 | 2.060 | 3 |
| 44.26 | 2.046 | 4 |
| 44.65 | 2.029 | 7 |
| 45.00 | 2.014 | 4 |
| 45.26 | 2.003 | 3 |
| 45.53 | 1.992 | 4 |
| 46.00 | 1.973 | 1 |
| 46.32 | 1.960 | 4 |
| 46.73 | 1.944 | 2 |
| 47.07 | 1.931 | 4 |
| 47.55 | 1.912 | 4 |
| 48.00 | 1.895 | 3 |
| 48.40 | 1.881 | 6 |
| 48.85 | 1.864 | 7 |
| 49.26 | 1.850 | 3 |
| 49.80 | 1.831 | 2 |

Chemical analysis of the crystalline product led to the following compositional figures:

| Composition | Wt. % | Mole Ratio on $Al_2O_3$ Basis |
|---|---|---|
| N | 0.48 | — |
| Na | 0.09 | — |
| $Al_2O_3$ | 2.61 | 1.0 |
| $SiO_2$ | 92.8 | 60.6 |
| $N_2O$ | | 2.13 |
| $Na_2O$ | | 0.08 |

Physical analysis of the crystalline product of Example 1 calcined 16 hours at 1000° F showed it to have a surface area of 218 m²/gram and adsorption tests (conducted as described hereinabove) produced the following results:

| Adsorption | Wt. % |
|---|---|
| Cyclohexane | 1.4 |
| n-Hexane | 5.3 |
| Water | 5.5 |

EXAMPLE 2

A batch of ZSM-23 was prepared by first forming a solution of 2.64 grams sodium aluminate (43.1% $Al_2O_3$, 33.1% $Na_2O$ and 24.7% $H_2O$), 48 grams $H_2O$ and 0.27 gram NaOH (50% solution with water). Then 28.8 grams of pyrrolidine were added to the above solution, followed by the addition of 132 grams of colloidal silica (30% $SiO_2$ and 70% $H_2O$). The resulting product was mixed until a homogeneous gel was formed. The gel was composed of the following components in mole ratios:

$R^+/(R^+ + M^+) = 0.93$, where M is sodium and $R^+$ is a nitrogen-containing cation derived from pyrrolidine $OH^-/SiO_2 = 0.048$ (not including any contribution of $OH^-$ from pyrrolidine)

$H_2O/OH^- = 246$ (not including any contribution of $OH^-$ from pyrrolidine)

$SiO_2/Al_2O_3 = 59.1$

The mixture was maintained at 350° F. for 7 days, during which time crystallization was complete. The product crystals were filtered out of solution and water washed continuously for approximately 16 hours and then dried at 230° F.

X-ray analysis of the crystalline product showed the crystals to have a diffraction pattern corresponding to Table I. Additional lines showing the presence of trace amounts of ZSM-5 were also observed.

Chemical analysis of the crystalline product led to the following compositional figures:

| Composition | Wt. % | Mole Ratio on $Al_2O_3$ Basis |
|---|---|---|
| N | 1.22 | — |
| Na | 0.14 | — |
| $Al_2O_3$ | 2.5 | 1.0 |
| $SiO_2$ | 92.9 | 63.3 |
| $N_2O$ | | 1.93 |
| $Na_2O$ | | 0.12 |

Physical analysis of the crystalline product after calcination at 1000° F for 16 hours showed it to have a surface area of 226 m²/gram and adsorption tests (conducted as described hereinabove) produced the following results:

| Adsorption | Wt. % |
|---|---|
| Cyclohexane | 1.7 |

| Adsorption | Wt. % |
|---|---|
| n-Hexane | 5.6 |
| Water | 6.2 |

EXAMPLE 3

A batch of ZSM-23 was prepared by first forming a solution of 2.64 grams sodium aluminate (43.1% $Al_2O_3$, 33.1% $Na_2O$ and 24.7% $H_2O$), 48 grams $H_2O$ and 0.27 gram NaOH (50% solution with water). Then 28.8 grams of pyrrolidine were added to the above solution, followed by the addition of 132 grams of colloidal silica (30% $SiO_2$ and 70% $H_2O$). The resulting product was mixed until a homogeneous gel was formed. The gel was composed of the following components in mole ratios:

$R^+/(R^+ + M^+) = 0.93$, where M is sodium and $R^+$ is a nitrogen-containing cation derived from pyrrolidine $OH^-/SiO = 0.048$ (not including any contribution of $OH^-$ from pyrrolidine)

$H_2O/OH^- = 249$ (not including any contribution $OH^-$ from pyrrolidine)

$SiO_2/Al_2O_3 = 59.2$

The mixture was maintained at 350° F for 11 days, during which time crystallization was complete. The product crystals were filtered out of solution and water washed continuously for approximately 16 hours and thereafter dried at 230° F.

X-ray analysis of the crystalline product showed the crystals to have the following diffraction pattern:

TABLE III

| 2θ | d(A) | I/I$_o$ |
|---|---|---|
| 7.90 | 11.19 | 38 |
| 8.75 | 10.11 | 20 |
| 9.23 | 9.58 | 5 |
| 11.22 | 7.89 | 16 |
| 11.85 | 7.47 | 3 |
| 14.30 | 6.19 | 2 |
| 14.50 | 6.11 | 4 |
| 14.70 | 6.03 | 3 |
| 15.51 | 5.71 | 4 |
| 15.80 | 5.61 | 6 |
| 16.10 | 5.50 | 3 |
| 16.25 | 5.45 | 5 |
| 17.20 | 5.16 | 1 |
| 17.80 | 4.98 | 5 |
| 18.10 | 4.90 | 11 |
| 19.60 | 4.53 | 51 |
| 20.00 | 4.44 | 9 |
| 20.83 | 4.26 | 70 |
| 21.40 | 4.15 | 11 |
| 21.69 | 4.10 | 17 |
| 21.91 | 4.06 | 30 |
| 22.78 | 3.90 | 100 |
| 23.28 | 3.82 | 19 |
| 23.87 | 3.73 | 77 |
| 24.55 | 3.63 | 58 |
| 25.18 | 3.54 | 34 |
| 25.85 | 3.45 | 42 |
| 26.50 | 3.36 | 6 |
| 26.90 | 3.31 | 7 |
| 28.19 | 3.17 | 8 |
| 28.90 | 3.09 | 1 |
| 29.29 | 3.05 | 6 |
| 29.58 | 3.02 | 1 |
| 29.95 | 2.983 | 5 |
| 31.38 | 2.851 | 9 |
| 31.64 | 2.828 | 4 |
| 32.15 | 2.784 | 2 |
| 32.95 | 2.718 | 1 |
| 33.95 | 2.640 | 4 |
| 34.55 | 2.596 | 2 |
| 35.39 | 2.536 | 28 |
| 36.00 | 2.495 | 8 |
| 36.40 | 2.468 | 7 |
| 37.13 | 2.421 | 4 |
| 37.53 | 2.396 | 6 |
| 38.45 | 2.341 | 8 |
| 39.04 | 2.307 | 3 |
| 40.10 | 2.249 | 1 |
| 40.50 | 2.227 | 1 |
| 41.00 | 2.201 | 2 |
| 41.30 | 2.186 | 1 |
| 41.58 | 2.172 | 1 |
| 42.29 | 2.137 | 1 |
| 42.60 | 2.122 | 1 |
| 43.56 | 2.078 | 3 |
| 44.13 | 2.052 | 4 |
| 44.66 | 2.029 | 7 |
| 45.22 | 2.005 | 2 |
| 45.56 | 1.991 | 3 |
| 46.33 | 1.960 | 4 |
| 46.74 | 1.943 | 1 |
| 47.09 | 1.930 | 2 |
| 47.44 | 1.916 | 4 |
| 47.87 | 1.900 | 3 |
| 48.33 | 1.883 | 4 |
| 48.92 | 1.862 | 7 |
| 49.55 | 1.840 | 1 |
| 49.83 | 1.830 | 2 |

Chemical analysis of the crystalline product led to the following compositional figures:

| Composition | Wt. % | Mole Ratio on $Al_2O_3$ Basis |
|---|---|---|
| N | 1.33 | — |
| Na | 0.12 | — |
| $Al_2O_3$ | 2.43 | 1.0 |
| $SiO_2$ | 96.2 | 67.3 |
| $N_2O$ | | 2.18 |
| $Na_2O$ | | 0.11 |

Physical analysis of the crystalline product after calcination for 16 hours at 1000° F showed it to have a surface area of 195 m$^2$/gram and adsorption tests (conducted as described hereinabove) produced the following results:

| Adsorption | Wt. % |
|---|---|
| Cyclohexane | 1.3 |
| n-Hexane | 5.6 |
| Water | 4.0 |

EXAMPLE 4

A batch of ZSM-23 was prepared by first forming a solution of 2.64 grams sodium aluminate (43.1% $Al_2O_3$, 33.1% $Na_2O$ and 24.7% $H_2O$), 48 grams $H_2O$ and 0.50 grams NaOH (50% solution with water). Then 20.0 grams of pyrrolidine were added to the above solution, followed by the addition of 132 grams of colloidal silica (30% $SiO_2$ and 70% $H_2O$). The resulting product was mixed until a homogeneous gel was formed. The gel was composed of the following components in mole ratios:

$R^+/(R^+ + M^+) = 0.89$ where M is sodium and $R^+$ is the nitrogen-containing cation derived from pyrrolidine $OH^-/SiO_2 = 0.053$ (not including any contribution of $OH^-$ from pyrrolidine)

$H_2O/OH^- = 228$ (not including any contribution of $OH^-$ from pyrrolidine)

$SiO_2/Al_2O_3 = 58.1$

The mixture was maintained at 350° F for 10 days, during which time crystallization was complete. The product crystals were filtered out of solution and water washed continuously for approximately 16 hours and then dried at 230° F.

X-ray analysis of the crystalline product showed the crystals to have a diffraction pattern corresponding to Table I. Additional lines showing the presence of trace amounts of ZSM-5 were also observed.

Chemical analysis of the crystalline product led to the following compositional figures:

| Composition | Wt. % | Mole Ratio on $Al_2O_3$ Basis |
|---|---|---|
| N | 1.21 | — |
| Na | 0.26 | — |
| $Al_2O_3$ | 2.53 | 1.0 |
| $SiO_2$ | 94.4 | 63.4 |
| $N_2O$ | | 1.92 |
| $Na_2O$ | | 0.23 |

Physical analysis of the crystalline product after calcination for 16 hours at 1000° F showed it to have a surface area of 199 m²/gram and adsorption tests (conducted as described hereinabove) produced the following results:

| Adsorption | Wt. % |
|---|---|
| Cyclohexane | 1.0 |
| n-Hexane | 5.7 |
| Water | 4.2 |

EXAMPLE 5

ZSM-23 was prepared by forming a solution of 2.64 grams sodium aluminate (43.1% $Al_2O_3$, 33.1% $Na_2O$ and 24.7% $H_2O$) and 50 grams $H_2O$. Then, 28.8 grams of pyrrolidine were added to this solution, followed by the addition of 132 grams of colloidal silica (30% $SiO_2$ and 70% $H_2O$). The resulting product was mixed until a homogeneous gel was formed. The gel was composed of the following components in mole ratios:

$R^+/(R^+ + M^+) = 0.94$ where M is sodium and $R^+$ is the nitrogen-containing cation derived from pyrrolidine $OH^-/SiO_2 = 0.042$ (not including any contribution of $OH^-$ from pyrrolidine)

$H_2O/OH^- = 282$ (not including any contribution of $OH^-$ from pyrrolidine)

$SiO_2/Al_2O_3 = 59.2$

The mixture was maintained at 350° F for 13 days, during which time crystallization was complete. The product crystals were filtered out of solution and water washed continuously for approximately 16 hours and then dried at 230° F.

X-ray analysis of the crystalline product showed the crystals to have a diffraction pattern corresponding to Table I. Additional lines showing the presence of ZSM-5 and alpha crystobalite were also observed.

Chemical analysis of the crystalline product led to the following compositional figures:

| Composition | Wt.% | Mole Ratio on $Al_2O_3$ Basis |
|---|---|---|
| N | 1.47 | — |
| Na | 0.13 | — |
| $Al_2O_3$ | 2.4 | 1.0 |
| $SiO_2$ | 94.2 | 66.8 |
| $N_2O$ | | 2.44 |
| $Na_2O$ | | 0.12 |

Physical analysis of the crystalline product after calcination for 16 hours at 1000° F showed it to have a surface area of 235 m²/gram and adsorption tests (conducted as described hereinabove) provided the following results:

| Adsorption | Wt.% |
|---|---|
| Cyclohexane | 1.7 |
| n-Hexane | 5.4 |
| Water | 3.2 |

EXAMPLE 6

ZSM-23 was prepared by forming a solution of 1.32 grams sodium aluminate (43.1% $Al_2O_3$, 33.1% $Na_2O$ and 24.7% $H_2O$), 0.14 gram NaOH (50% solution with water) and 60 grams of $H_2O$ containing 0.1 weight percent of a surfactant, i.e. 2,4,7,9-tetramethyl-5-decyn-4,7-diol. Then, 14.4 grams of pyrrolidine were added to the above solution, followed by the addition of 66 grams of colloidal silica (30% silica and 70% $H_2O$). The resulting product was mixed until a homogeneous gel was formed. The gel was composed of the following components in mole ratios:

$R^+/R^+ + M^+ = 0.94$, where M is sodium and $R^+$ is the nitrogen-containing cation derived from pyrrolidine $OH^-/SiO_2 = 0.044$ (not including any contribution of $OH^-$ from pyrrolidine)

$H_2O/OH^- = 408$ (not including any contribution of $OH^-$ from pyrrolidine)

$SiO_2/Al_2O_3 = 64.7$

The mixture was maintained at 350° F for 10 days, during which time crystallization was complete. The product crystals were filtered out of solution and water washed continuously for approximately 16 hours and then dried at 230° F.

X-ray analysis of the crystalline product showed the crystals to have the following diffraction pattern:

TABLE IV

| 2θ | d(A) | I/I₀ |
|---|---|---|
| 7.74 | 11.42 | 20 |
| 8.03 | 11.01 | 45 |
| 8.76 | 10.09 | 18 |
| 9.25 | 9.56 | 6 |
| 11.26 | 7.86 | 18 |
| 14.57 | 6.08 | 4 |
| 15.53 | 5.71 | 2 |
| 15.87 | 5.58 | 4 |
| 16.31 | 5.43 | 8 |
| 17.26 | 5.14 | 1 |
| 17.70 | 5.01 | 3 |
| 18.10 | 4.90 | 12 |
| 18.89 | 4.70 | 2 |
| 19.60 | 4.53 | 60 |
| 20.02 | 4.44 | 18 |
| 20.41 | 4.35 | 11 |
| 20.84 | 4.26 | 75 |
| 21.41 | 4.15 | 26 |
| 21.66 | 4.10 | 27 |
| 21.93 | 4.05 | 21 |
| 22.76 | 3.91 | 100 |
| 23.48 | 3.79 | 19 |
| 23.95 | 3.72 | 79 |

TABLE IV-continued

| 2θ | d(A) | I/I$_o$ |
|---|---|---|
| 24.57 | 3.62 | 71 |
| 25.20 | 3.53 | 40 |
| 25.87 | 3.44 | 45 |
| 26.61 | 3.35 | 7 |
| 27.00 | 3.30 | 8 |
| 28.25 | 3.16 | 11 |
| 28.88 | 3.09 | 2 |
| 29.34 | 3.04 | 6 |
| 29.92 | 2.986 | 5 |
| 31.55 | 2.836 | 10 |
| 32.19 | 2.781 | 2 |
| 33.00 | 2.714 | 1 |
| 34.02 | 2.635 | 4 |
| 34.52 | 2.598 | 2 |
| 35.45 | 2.532 | 29 |
| 35.95 | 2.498 | 9 |
| 36.40 | 2.468 | 13 |
| 37.03 | 2.428 | 3 |
| 37.56 | 2.395 | 5 |
| 38.55 | 2.335 | 9 |
| 41.00 | 2.201 | 1 |
| 43.64 | 2.074 | 4 |
| 44.23 | 2.048 | 4 |
| 44.75 | 2.025 | 6 |
| 45.57 | 1.991 | 2 |
| 46.46 | 1.954 | 3 |
| 47.24 | 1.924 | 3 |
| 47.73 | 1.905 | 4 |
| 48.34 | 1.883 | 4 |
| 49.02 | 1.858 | 7 |
| 49.76 | 1.832 | 1 |

Chemical analysis of the crystalline product led to the following compositional figures:

| Composition | Wt. % | Mole Ratio on Al$_2$O$_3$ Basis |
|---|---|---|
| N | 1.27 | |
| Na | 0.20 | |
| Al$_2$O$_3$ | 2.89 | 1.0 |
| SiO$_2$ | 93.7 | 55.1 |
| N$_2$O | | 1.73 |
| Na$_2$O | | 0.15 |

Physical analysis of the crystalline product after calcination for 16 hours at 1000° F showed it to have a surface area of 213 m$^2$/gram and adsorption tests (conducted as described hereinabove) provided the following results:

| Adsorption | Wt. % |
|---|---|
| Cyclohexane | 2.2 |
| n-Hexane | 4.5 |
| Water | 5.1 |

EXAMPLE 7

ZSM-23 was prepared by forming a solution of 18.5 grams sodium aluminate (43.1% Al$_2$O$_3$, 33.1% Na$_2$O and 24.7% H$_2$O), 1.9 grams NaOH (50% solution with water) and 560 grams H$_2$O. Then, 201.6 rams of pyrrolidine were added to the above solution, followed by the addition of 924 grams of colloidal silica (30% silica and 70% H$_2$O). The resulting product was mixed until a homogeneous gel was formed. The gel was composed of the following components in mole ratios:

R$^+$/(R$^+$ + M$^+$) = 0.93, where M is sodium and R$^+$ is a nitrogen-containing cation derived from pyrrolidine OH$^-$/SiO$_2$ = 0.048 (not including any contribution of OH$^-$ from pyrrolidine)

H$_2$O/OH$^-$ = 304 (not including any contribution of OH$^-$ from pyrrolidine)

SiO$_2$/Al$_2$O$_3$ = 59.2

The mixture was maintained at 350° F for 11 days, during which time crystallization was complete. The product crystals were filtered out of solution and water washed continuously for approximately 16 hours and then dried at 230° F.

X-ray analysis of the crystalline product showed the crystals to have the following diffraction pattern:

TABLE V

| 2θ | d(A) | I/I$_o$ |
|---|---|---|
| 7.88 | 11.22 | 30 |
| 8.09 | 10.93 | 27 |
| 8.74 | 10.12 | 18 |
| 11.22 | 7.89 | 18 |
| 11.83 | 7.48 | 2 |
| 12.43 | 7.12 | 1 |
| 13.15 | 6.73 | 1 |
| 13.85 | 6.39 | 1 |
| 14.55 | 6.09 | 4 |
| 14.76 | 6.00 | 1 |
| 15.55 | 5.70 | 2 |
| 15.85 | 5.59 | 3 |
| 16.27 | 5.45 | 6 |
| 17.22 | 5.15 | 2 |
| 17.71 | 5.01 | 4 |
| 18.05 | 4.91 | 12 |
| 19.61 | 4.53 | 55 |
| 20.03 | 4.43 | 12 |
| 20.85 | 4.26 | 76 |
| 21.38 | 4.16 | 20 |
| 21.69 | 4.10 | 12 |
| 21.90 | 4.06 | 33 |
| 22.78 | 3.90 | 100 |
| 23.28 | 3.82 | 12 |
| 23.90 | 3.72 | 80 |
| 24.56 | 3.62 | 63 |
| 25.15 | 3.54 | 35 |
| 25.88 | 3.44 | 45 |
| 26.60 | 3.35 | 10 |
| 26.93 | 3.31 | 5 |
| 27.40 | 3.25 | 1 |
| 28.20 | 3.16 | 9 |
| 28.92 | 3.09 | 2 |
| 29.30 | 3.05 | 6 |
| 29.90 | 2.988 | 5 |
| 30.29 | 2.951 | 1 |
| 30.87 | 2.897 | 2 |
| 31.48 | 2.842 | 12 |
| 31.90 | 2.805 | 2 |
| 32.20 | 2.780 | 2 |
| 32.95 | 2.718 | 1 |
| 33.99 | 2.637 | 4 |
| 34.34 | 2.611 | 1 |
| 35.40 | 2.536 | 27 |
| 36.05 | 2.491 | 7 |
| 36.41 | 2.468 | 14 |
| 37.15 | 2.420 | 1 |
| 37.50 | 2.398 | 6 |
| 38.48 | 2.339 | 10 |
| 39.21 | 2.298 | 2 |
| 40.22 | 2.242 | 1 |
| 40.59 | 2.223 | 1 |
| 41.00 | 2.201 | 1 |
| 41.55 | 2.173 | 1 |
| 42.08 | 2.147 | 1 |
| 42.35 | 2.134 | 1 |
| 42.59 | 2.123 | 1 |
| 43.58 | 2.077 | 3 |
| 44.10 | 2.053 | 2 |
| 44.60 | 2.032 | 7 |
| 45.15 | 2.008 | 1 |
| 45.49 | 1.994 | 2 |
| 46.38 | 1.958 | 3 |
| 47.20 | 1.926 | 3 |
| 47.70 | 1.906 | 4 |
| 48.38 | 1.881 | 4 |
| 48.91 | 1.862 | 7 |
| 49.71 | 1.834 | 1 |

Chemical analysis of the crystalline product led to the following compositional figures:

| Composition | Wt. % | Mole Ratio on Al$_2$O$_3$ Basis |
|---|---|---|
| N | 1.34 | — |
| Na | 0.09 | — |

-continued

| Composition | Wt. % | Mole Ratio on Al₂O₃ Basis |
|---|---|---|
| Al₂O₃ | 2.46 | 1.0 |
| SiO₂ | 97.6 | 67.9 |
| N₂O | | 2.08 |
| Na₂O | | 0.08 |

Physical analysis of the crystalline product after calcination for 16 hours at 1000° F showed it to have a surface area of 160 m²/gram and adsorption tests (conducted as described hereinabove) provided the following results:

| Adsorption | Wt. % |
|---|---|
| Cyclohexane | 1.4 |
| n-Hexane | 5.1 |
| Water | 5.0 |

EXAMPLE 8

ZSM-23 was prepared by forming a solution of 13.2 grams sodium aluminate (43.1% Al₂O₃, 33.1% Na₂O and 24.7% H₂O), 2.72 grams NaOH (50% solution with water) and 240 grams H₂O. Then, 145.6 grams of pyrrolidine were added, followed by the addition of 1318 grams of colloidal silica (30% silica and 70% H₂O). The resulting product was mixed until a homogeneous gel was formed. The gel was composed of the following components in mole ratios:

$R^+/(R^+ + M^+) = 0.92$, where M is sodium and $R^+$ is the nitrogen-containing cation derived from pyrrolidine $OH^-/SiO_2 = 0.0265$ (not including any contribution of $OH^-$ from pyrrolidine)

$H_2O/OH^- = 371$ (not including any contribution of $OH^-$ from pyrrolidine)

$SiO_2/Al_2O_3 = 118$

The mixture was stirred at 350° F for 2 days, during which time crystallization was complete. The product crystals were filtered out of solution and water washed continuously for approximately 16 hours and then dried at 230° F.

X-ray analysis of the crystalline product showed the crystals to have a diffraction pattern corresponding to Table I. Additional lines showing the presence of trace amounts of unidentified crystalline material were also observed.

Chemical analysis of the crystalline product led to the following compositional figures:

| Composition | Wt. % | Mole Ratio on Al₂O₃ Basis |
|---|---|---|
| C | 4.96 | — |
| N | 1.11 | — |
| Na | 0.27 | — |
| Al₂O₃ | 1.65 | 1.0 |
| SiO₂ | 96.9 | 101 |
| N₂O | | 2.68 |
| Na₂O | | 0.36 |

Physical analysis of the crystalline product after calcination for 16 hours at 1000° F showed it to have a surface area of 215 m²/gram and adsorption tests (conducted as described hereinabove) provided the following results:

| Adsorption | Wt. % |
|---|---|
| Cyclohexane | 2.1 |
| n-Hexane | 6.1 |
| Water | 4.6 |

EXAMPLE 9

ZSM-23 was prepared by forming a solution of 6.6 grams sodium aluminate (43.1% Al₂O₃, 33.1% Na₂O and 24.7% H₂O), 2.72 grams NaOH (50% solution with water) and 240 grams H₂O. Then, 145.6 grams of pyrrolidine were added, followed by the addition of 1318 grams of colloidal silica (30% silica and 70% H₂O). The resulting product was mixed until a homogeneous gel was formed. The gel was composed of the following components in mole ratios:

$R^+/(R^+ + M^+) = 0.95$, where M is sodium and $R^+$ is the nitrogen-containing cation derived from pyrrolidine $OH^-/SiO_2 = 0.016$ (not including any contribution of $OH^-$ from pyrrolidine)

$H_2O/OH^- = 620$ (not including any contribution of $OH^-$ from pyrrolidine)

$SiO_2/Al_2O_3 = 236$

The mixture was stirred at 350° for 5 days, during which time crystallization was complete. The product crystals were filtered out of solution and water washed continuously for approximately 16 hours and then dried at 230° F.

X-ray analysis of crystalline product showed the crystals to have a diffraction pattern corresponding to Table I. The presence of alpha crystobalite was also observed.

Chemical analysis of the crystalline product led to the following compositional figures:

| Composition | Wt. % | Mole Ratio on Al₂O₃ Basis |
|---|---|---|
| N | 0.52 | — |
| Na | 0.09 | — |
| Al₂O₃ | 0.73 | 1.0 |
| SiO₂ | 93.5 | 217 |
| N₂O | | 2.75 |
| Na₂O | | 0.26 |

Physical analysis of the crystalline product after calcination for 16 hours at 1000° F showed it to have a surface area of 72 m²/gram and adsorption tests (conducted as described hereinabove) provided the following results:

| Adsorption | Wt. % |
|---|---|
| Cyclohexane | 1.2 |
| n-Hexane | 2.0 |
| Water | 2.3 |

EXAMPLE 10

Twenty-five grams of ZSM-23, prepared as described in Example 1, were contacted five times at 210° F with a 5 weight percent solution of NH₄Cl, each contact being for a period of 1 hour. The resulting product having a sodium content of 0.05 weight percent was calcined for 10 hours at 1000° F.

Propylene at 1 liter/hour was passed over 0.25 gram of the above catalyst at 600° F and atmospheric pressure. Effluent collected between 1 and 2 hours on stream and analyzed showed oligomerization (polymerization) of the propylene charge in an amount corresponding to 84.8 weight percent of the liquid product and aromatization of the propylene charge in an amount corresponding to 18.4 weight percent of the liquid product.

EXAMPLE 11

Twenty grams of ZSM-23, prepared as described in Example 5, were contacted five times at 210° F with a 5 weight percent solution of $NH_4Cl$, each contact being for a period of 1 hour. The resulting product having a sodium content of 0.05 weight percent was calcined for 10 hours at 1000° F.

The resulting catalyst was subjected to the alpha test described by P. B. Weisz and J. N. Miale in *Journal of Catalysis* 4,527–529 (1965) to determine cracking rate of n-hexane with the liquid hourly space velocity maintained at 3.37 and the temperature maintained at 700° F. The n-hexane cracking rate α, 5 minutes and 25 minutes after commencement of flow was 310 and 302 respectively, indicating the cracking activity of the prepared catalyst.

EXAMPLE 12

69.7 grams of ZSM-23, prepared as described in Example 8, were heat treated for 3 hours at 1000° F in nitrogen and then contacted four times at 180°–200° F with a 10 weight percent solution of $NH_4Cl$, each contact being for a period of 2 hours. The resulting product having a sodium content of 0.03 weight percent was calcined for 10 hours at 1000° F and thereafter steamed for 20 hours at 1100° F.

The resulting catalyst was contacted with a charge of dimethyl ether at a temperature of 600° F utilizing a WHSV of 1.15 to obtain a conversion of 26.8 percent to hydrocarbons and water. Analysis of the hydrocarbon product obtained showed the following weight percent:

$C_5^+$: 36.1
$C_1$: 11.7
$C_2^=$: 22.0
$C_2$: 1.6
$C_3^=$: 14.6
$C_3$: 3.4
i-$C_4$: 6.3
$C_4^=$: 4.3
n $C_4$: 0

EXAMPLE 13

Propylene at 1 liter/hour was passed over 0.25 gram of a catalyst, prepared as in Example 12, at 600° F and atmospheric pressure. Effluent collected between 1 and 2 hours on stream and analyzed showed oligomerization of the propylene charge with the following product analysis in weight percent:

$C_5^+$: 80.9
$C_1$: 4.4
$C_2^=$: 0.9
$C_2$: 0.6
$C_3^=$: 3.9
$C_3$: 2.4
$C_4^=$: 5.9
$C_4$: 0.9

These data show a high yield of a $C_5^+$ gasoline fraction.

We claim:

1. A synthetic crystalline aluminosilicate zeolite having a composition in the anhydrous state, expressed in terms of mole ratios of oxides, as follows:

$$(0.58-3.4)M_2O : Al_2O_3 : (40-250) SiO_2$$

wherein M is at least one cation having a valence n, said zeolite having the X-ray diffraction lines of Table I of the specification.

2. A crystalline aluminosilicate zeolite resulting from thermal treatment of the composition of claim 1.

3. A synthetic crystalline aluminosilicate zeolite according to claim 1 having a composition in the anhydrous state, expressed in terms of mole ratios of oxides, as follows:

$$(0.5-3.0)R_2O : (0.08-0.4)M_2O : Al_2O_3 : (40-250) SiO_2$$

wherein R is a nitrogen-containing organic cation and M is an alkali metal cation.

4. A synthetic crystalline aluminosilicate zeolite according to claim 3 having a composition in the anhydrous state, expressed in terms of mole ratios of oxides, as follows:

$$(0.7-2.8)R_2O : (0.08-0.25)M_2O : Al_2O_3 : (50-220) SiO_2.$$

5. A synthetic crystalline aluminosilicate zeolite according to claim 3 wherein M is sodium.

6. A synthetic crystalline aluminosilicate zeolite according to claim 4 wherein M is sodium.

7. The synthetic crystalline aluminosilicate zeolite according to claim 3 wherein R is the nitrogen-containing organic cation derived from pyrrolidine.

8. The synthetic crystalline aluminosilicate zeolite according to claim 7 wherein M is sodium.

9. The synthetic crystalline aluminosilicate zeolite resulting from thermal treatment of the composition of claim 7.

10. A method for preparing the crystalline aluminosilicate zeolite defined in claim 1 which comprises preparing a mixture containing sources of an alkali metal oxide, an oxide of aluminum, an oxide of silicon, a nitrogen-containing organic cation and water and having a composition, in terms of mole ratios of oxides, falling within the following ranges:

$R+/(R+ + M+)$ : 0.85–0.95
$OH-/SiO_2$ : 0.01–0.049
$H_2O/OH-$ : 200–600
$SiO_2/Al_2O_3$ : 55–70 wherein R is a nitrogen-containing cation derived from pyrrolidine and M is an alkali metal ion, maintaining the mixture at a temperature of above 280° F until the crystals of said aluminosilicate are formed.

11. The method of claim 10 wherein the temperature is maintained between about 280° F and about 400° F.

12. The method of claim 11 wherein the temperature is maintained between about 300° F and about 375° F.

13. A synthetic crystalline aluminosilicate zeolite comprising the zeolite of claim 1 having its original cations replaced, at least in part, with a cation or a mixture of cations selected from the group consisting of hydrogen and hydrogen precursors, rare earth metals and metals from Groups IIA, IIIA, IVA, IB, IIB, IIIB, IVB, VIB and VIII of the Periodic Table of Elements.

14. A synthetic crystalline aluminosilicate zeolite comprising the zeolite of claim 2 having its original cations replaced, at least in part, with a cation or a mixture of cations selected from the group consisting of hydrogen and hydrogen pressure, rare earth metals and metals from Groups IIA, IIIA, IVA, IB, IIB, IIIB, IVB, VIB and VIII of the Periodic Table of the Elements.

15. A synthetic crystalline aluminosilicate zeolite comprising the zeolite of claim 3 having its original cations replaced, at least in part, with a cation or a mixture of cations selected from the group consisting of hydrogen and hydrogen precursors, rare earth metals and metals from Groups IIA, IIIA, IVA, IB, IIB, IIIB, IVB, VIB and VIII of the Periodic Table of the Elements.

16. A synthetic crystalline aluminosilicate zeolite comprising the zeolite of claim 4 having its original cations replaced, at least in part, with a cation or a mixture of cations selected from the group consisting of hydrogen and hydrogen precursors, rare earth metals and metals from Groups IIA, IIIA, IVA, IB, IIB, IIIB, IVB, VIB and VIII of the Periodic Table of the Elements.

17. A synthetic crystalline aluminosilicate zeolite comprising the zeolite of claim 7 having its original cations replaced, at least in part, with a cation or a mixture of cations selected from the group consisting of hydrogen and hydrogen precursors, rare earth metals and metals from Groups IIA, IIIA, IVA, IB, IIB, IIIB, IVB, VIB and VIII of the Periodic Table of the Elements.

18. The synthetic crystalline aluminosilicate zeolite of claim 15 wherein said replacing cation is hydrogen or a hydrogen precursor.

19. The synthetic aluminosilicate zeolite resulting from heating the composition of claim 15 at a temperature of from about 200° C to about 900° C.

20. The synthetic aluminosilicate zeolite resulting from heating the composition of claim 16 at a temperature of from about 200° C to about 900° C.

21. The synthetic aluminosilicate zeolite resulting from heating the composition of claim 17 at a temperature of from about 200° C to about 900° C.

* * * * *

UNITED STATES PATENT AND TRADEMARK OFFICE
CERTIFICATE OF CORRECTION

PATENT NO. : 4,076,842
DATED : February 28, 1978
INVENTOR(S) : Charles J. Plank, Edward J. Rosinski and Mae K. Rubin It is certified that error appears in the above-identified patent and that said Letters Patent are hereby corrected as shown below:

Column 1, line 40, "Ca, Sr" should read -- $\frac{Ca}{2}, \frac{Sr}{2}$ --.

Column 2, line 39, "IVD" should read -- IVB --.

Column 3, line 12, "perpendicular" should be -- particular --.

Column 3, line 48, "or" (second occurrence) should be -- of --.

Column 3, line 56, "meal" should be -- metal --.

Column 4, line 9, "R+/R+ + M+)" should read -- $\frac{R^+}{R^+ + M^+}$ --.

Column 13, line 55, "rams" should read -- grams --.

Column 18, line 5, "M2O" should read -- $\frac{M_2O}{n}$ --.

Column 19, line 5, "pressure" should be -- precursors --.

Signed and Sealed this

Twenty-fifth Day of July 1978

[SEAL]

Attest:

RUTH C. MASON
Attesting Officer

DONALD W. BANNER
Commissioner of Patents and Trademarks